(12) United States Patent
Trost et al.

(10) Patent No.: US 11,534,393 B2
(45) Date of Patent: Dec. 27, 2022

(54) COMPOSITIONS HAVING GINGER-CURCUMIN AND CERTAIN ADDITIVES

(71) Applicants: Paul B. Trost, Golden, CO (US); Joyce A. Trost, Estero, FL (US)

(72) Inventors: Paul B. Trost, Golden, CO (US); Joyce A. Trost, Estero, FL (US)

( * ) Notice: Subject to any disclaimer, the term of this patent is extended or adjusted under 35 U.S.C. 154(b) by 0 days.

(21) Appl. No.: 16/875,648

(22) Filed: May 15, 2020

(65) Prior Publication Data
US 2020/0276105 A1   Sep. 3, 2020

Related U.S. Application Data

(63) Continuation of application No. 15/273,974, filed on Oct. 3, 2017, now Pat. No. 10,653,617.

(60) Provisional application No. 62/543,799, filed on Aug. 10, 2017, provisional application No. 62/496,112, filed on Oct. 5, 2016.

(51) Int. Cl.

| | |
|---|---|
| *A61K 8/9794* | (2017.01) |
| *A61K 31/255* | (2006.01) |
| *A61K 8/64* | (2006.01) |
| *A61K 8/46* | (2006.01) |
| *A61K 8/67* | (2006.01) |
| *A61K 8/73* | (2006.01) |
| *A61Q 19/08* | (2006.01) |
| *A61K 9/00* | (2006.01) |
| *A61K 36/9068* | (2006.01) |
| *A61K 31/12* | (2006.01) |
| *A61K 38/06* | (2006.01) |
| *A61K 31/10* | (2006.01) |
| *A61K 31/375* | (2006.01) |
| *A61K 31/728* | (2006.01) |
| *A61K 8/35* | (2006.01) |
| *A61P 17/02* | (2006.01) |
| *A61K 36/9066* | (2006.01) |

(52) U.S. Cl.
CPC .............. *A61K 8/9794* (2017.08); *A61K 8/35* (2013.01); *A61K 8/46* (2013.01); *A61K 8/463* (2013.01); *A61K 8/64* (2013.01); *A61K 8/676* (2013.01); *A61K 8/735* (2013.01); *A61K 9/0014* (2013.01); *A61K 31/10* (2013.01); *A61K 31/12* (2013.01); *A61K 31/255* (2013.01); *A61K 31/375* (2013.01); *A61K 31/728* (2013.01); *A61K 36/9066* (2013.01); *A61K 36/9068* (2013.01); *A61K 38/063* (2013.01); *A61P 17/02* (2018.01); *A61Q 19/08* (2013.01)

(58) Field of Classification Search
None
See application file for complete search history.

(56) References Cited

U.S. PATENT DOCUMENTS

| | | | |
|---|---|---|---|
| 9,265,792 B2 | 2/2016 | Riley | |
| 9,511,034 B1 | 12/2016 | Garrett | |
| 10,806,790 B1 * | 10/2020 | Shapiro | ............... A61K 31/435 |
| 2010/0105644 A1 | 4/2010 | Varani et al. | |
| 2012/0289597 A1 * | 11/2012 | Farber | .................. A61K 31/223 |
| | | | 514/551 |
| 2014/0328956 A1 | 11/2014 | Varani et al. | |

* cited by examiner

*Primary Examiner* — Susan Hoffman
(74) *Attorney, Agent, or Firm* — Thompson Coburn LLP; William A. Holtz

(57) ABSTRACT

A topical composition comprising ginger, curcumin, one or more of glutathione, MSM, Vitamin C, hyaluronic acid, sodium lauryl sulfate, Vitamin D and Vitamin E, and a carrier, wherein each of the glutathione, MSM, Vitamin C, hyaluronic acid, sodium lauryl sulfate, Vitamin D, and Vitamin E. When applied to human skin or animal skin, the composition can improve the appearance of skin and speed up wound healing.

24 Claims, 8 Drawing Sheets

COMPOSITIONS HAVING GINGER-CURCUMIN AND CERTAIN ADDITIVES

CROSS-REFERENCE

This application is a continuation of U.S. patent application Ser. No. 15/723,974, filed Oct. 3, 2017, which will issue as U.S. Pat. No. 10,653,617, which claims the benefit of U.S. provisional application 62/496,112, filed Oct. 5, 2016, and U.S. provisional application 62/543,799, filed Aug. 10, 2017, each of which are incorporated herein by reference in their entirety.

BACKGROUND

Human skin ages. During the aging process the skin experiences cellular breakdown resulting in a loss of thickness, formation of purpura (purple bruising), ease of tearing, and difficulty in wound healing, e.g., due to loss of collagen and fibroblasts.

Aging of the skin is exasperated by exposure to the sun's ultraviolet radiation. Such exposure facilitates the production of free radicals especially reactive oxygen species (ROS). These ROS species expedite the aging processes of the skin and collagen breakdown.

Cause of skin aging at the cellular level is a loss of connectivity by the collagen-stabilized fibroblast cells which connect each skin cell to the adjacent skin cells, and the subsequent formation of metalloproteinase-9. Collagen typically has the highest concentration of any protein found within the human body. Collagen is composed of three amino acid chains, bound together by sulfur.

Certain compounds, such as retinoids in pharmaceutical concentrations, have been historically used to help alleviate these conditions. Unfortunately, retinoid compounds present difficulties to the skin such as inflammation (redness), and burning and peeling when used in higher concentrations.

Low non-pharmaceutical concentrations of trans Retinol and Tetinolaldehyde are commonly utilized in Over the Counter (OTC) ointments, lotions and salves and claim to support collagen and procollagen production while suppressing collagen breakdown within the human body. However, the results are minimally effective.

SUMMARY

This disclosure is directed compounds and compositions, particularly topical compounds for human and animal (e.g., mammal) skin rejuvenation and wound healing by stimulating new growth of collagen and fibroblasts and inhibiting and/or decreasing the level of matrix metalloproteinase-1 (MMP-1) in the skin.

The compounds or compositions include a therapeutically effective amount of ginger and curcumin. Combined with the ginger-curcumin is at least one of hyaluronic acid, glutathione, methylsulfonylmethane (MSM), Vitamin C (ascorbic acid), sodium lauryl sulfate, Vitamin D and Vitamin E. In some formulations, only one of these additives is present, in other formulations two of these additives are present, in other formulations three of these additives are present, in other formulations four or five of these additives are present, and yet in other formulations all of these additives are present. In certain formulations, at least one of hyaluronic acid, glutathione, methylsulfonylmethane (MSM), Vitamin C, and sodium lauryl sulfate is present together with one or both of Vitamin D and Vitamin E.

Compounds according to this disclosure have shown accelerated growth of collagen, growth of fibroblasts, and decrease in the collagen-inhibiting MMP-1 enzyme compared to other ginger-curcumin compounds.

The amount of these additive(s) is at least 0.005 wt-% of the total composition; in some implementations, the amount of each of the additives present is at least 0.005 wt-%. In some implementations, the amount of all additives is no more than 15 wt-% of the composition, whereas in other implementations the amount of each additive is no more than 15 wt-% of the composition. In some implementations, the amount of each of ginger and curcumin is about 0.01-15 wt-% of the total composition.

One particular implementation disclosed herein is a topical composition for application to human skin. The composition comprises ginger; curcumin; one or more of glutathione, MSM, Vitamin C, hyaluronic acid, sodium lauryl sulfate, Vitamin D and Vitamin E; and a carrier. Each of the glutathione, MSM, Vitamin C, hyaluronic acid, sodium lauryl sulfate, Vitamin D, and Vitamin E, if present, is individually present at a concentration of 0.005-15 wt-% of the total composition.

Compounds including Vitamin D are especially useful for animal (non-human) applications, since many animals do not produce their own Vitamin D by exposure to the sun as opposed to humans.

Another particular implementation disclosed herein is a method for improving the appearance of human skin by topically applying a composition to the skin. Wrinkles are reduced, both in their depth (severity) and their number. The composition comprises ginger; curcumin; one or more of glutathione, MSM, Vitamin C, hyaluronic acid, sodium lauryl sulfate, Vitamin D and Vitamin E; and a carrier.

Also disclosed is a method for speeding wound healing by applying a composition to the wound.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. These and various other features and advantages will be apparent from a reading of the following detailed description.

DETAILED DESCRIPTION

DETAILED DESCRIPTION

Figure 1:
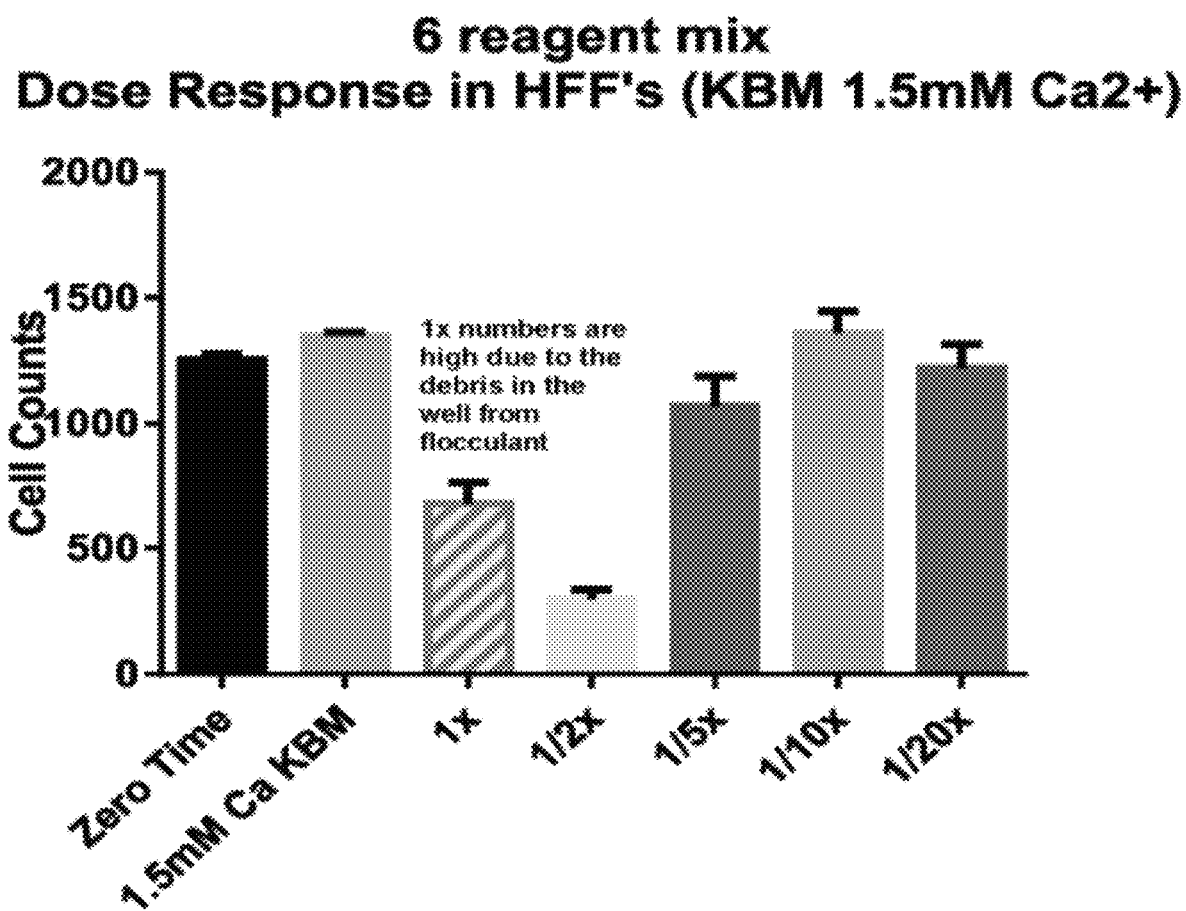
FIG. 1 is a graphical representation of a titration curve for a fibroblast cytotoxicity assay.

Ginger and curcumin, which are naturally occurring products, are natural alternatives to synthetic products and to pharmaceutical concentrations of Retin A. The combination of ginger and curcumin, when present in a topical composition, has been found to be as efficient at helping to alleviate skin-aging and improve a wound healing process as retinoids but without the burning/peeling side effects common with retinoid products.

However, the combination of ginger and curcumin is not without its negative factors. For example, a topical composition having ginger and curcumin in a carrier, (1) has a very slow uptake of the ginger-curcumin mixture into the skin, (2) promotes drying of the skin, (3) has difficulty in achieving a uniform mode of application, (4) may result in discoloration of the skin due to curcumin's yellow coloration, (5) continual application of the composition is recommended, due to the degradation of curcumin during the formation of collagen, (6) the combination of ginger-curcumin does not provide a source of sulfur to facilitate collagen production, and (7) curcumin is not stable under alkaline conditions. The additives disclosed herein enhance the formation of collagen and fibroblasts and decrease the MMP-1 enzyme that impedes collagen formation.

Although the term "ginger" is used herein, the ginger may be present as ginger, ginger extract(s), gingerol (e.g., 6-gingerol, 8-gingerol, 10-gingerol), analogs (e.g., 6-paradol, 6-shagoal, cassumunin) or other forms of the ginger molecule or analogs.

Although the term "curcumin" is used, the curcumin may be any or all of curcumin or its extract(s), demethoxycurcumin, bisdemethoxycurcumin or any of the analogs of curcumin. The curcumin may be synthetically produced or can be naturally derived, for example from turmeric. One specific curcumin is (1E,6E)-1,7-bis(4-hydroxy-3-methoxyphenyl)hepta-1,6-diene-3,5-dione. Alternately, tetrohydrocurcumin, a derivative of curcumin, may also be used.

Applicant found that by including at least one of hyaluronic acid, glutathione, methylsulfonylmethane (MSM), sodium lauryl sulfate (SLS), Vitamin C (ascorbic acid), Vitamin D and Vitamin E to a ginger-curcumin composition for topical use further increases the beneficial effects of the ginger-curcumin. In some formulations, only one of these additives is present, in other formulations two of these additives are present, in other formulations three of these additives are present, in other formulations four of these additives are present, and yet in other formulations all of these additives are present. A combination of hyaluronic acid, methylsulfonylmethane (MSM), sodium lauryl sulfate (SLS) and Vitamin C (ascorbic acid) increases procollagen and decreases the concentration of the MMP-1 enzyme, which impeded collagen formation. The efficiency of these additives with ginger and curcumin has been tested and found to increase viability and formation of fibroblasts, as compared to only ginger and curcumin. In some implementations, these four additives, even without ginger and curcumin, may increase procollagen, decrease the concentration of the MMP-1 enzyme, and produce other beneficial results. Addition of any of glutathione, Vitamin D and Vitamin E may further increase the beneficial results.

In certain formulations, at least one of hyaluronic acid, glutathione, methylsulfonylmethane (MSM), Vitamin C, and sodium lauryl sulfate is present together with one or both of Vitamin D and Vitamin E. In certain formulations, at least one of the sulfur-containing additives (glutathione, methylsulfonylmethane (MSM), sodium lauryl sulfate (SLS)) is combined with one or both of Vitamin D and Vitamin E.

When combined with ginger-curcumin, these additives provide various beneficial and synergistic results.

Hyaluronic acid, also known as hyaluronan, is naturally occurring in the human body in connective and epithelial tissue, and is known to contribute significantly to cell growth. Subcutaneously, hyaluronic acid facilitates the growth of collagen and connective tissue and increases the biological activity of newly formed collagen. Additionally, hyaluronic acid, applied topically, moisturizes the skin and is quickly adsorbed by the skin. Hyaluronic acid increases the effectiveness of the ginger-curcumin in the formation of collagen and procollagen, as compared to the ginger-curcumin alone.

Glutathione, when mixed with the ginger-curcumin, provides the skin with an absorbable form of sulfur having a valence of −2. Collagen is composed of numerous amino acids, especially cysteine and methionine, which benefit from the presence of sulfur. Furthermore, the intermediate products of collagen formation, such as peptides and proteins, containing cysteine and methionine, require the presence of sulfur. Glutathione thus provides an immediately available, and local source, of sulfur at valence −2, thereby facilitating more rapid formation of cysteine and methionine, which are basic building blocks of the collagen. Similar to hyaluronic acid, glutathione increases the effectiveness of the ginger-curcumin in the formation of collagen and procollagen, as compared to the ginger-curcumin alone.

MSM (methylsulfonylmethane) is naturally found in both plants and humans and includes sulfur. MSM is also a source of sulfur to facilitate the production of the amino acids cysteine and methionine, which aid in the formation of new procollagen and collagen. Specifically, MSM is a source of +6 sulfur. Sulfur is used in the alpha 2 collagen chain in a collagen triple helix. Thus, MSM provides a second biosynthetic, and local source, pathway to collagen formation.

Presence of the two alternative sources of sulfur (glutathione's −2 valence state and MSM's+6 valence state) will therefore synergistically aid in collagen formation due to different biosynthetic pathways, particularly in the presence of curcumin.

Sodium lauryl sulfate (SLS), also known as sodium dodecyl sulfate, has also been observed to facilitate the absorption of the ginger-curcumin complexes into the skin due to increasing the solubility of the curcumin within the skin. Other common detergent-type compounds may also be used to facilitate adsorption of the additives and/or ginger and/or curcumin into the skin.

Vitamin C is an antioxidant and provides free radical scavenging; curcumin is also an antioxidant. During the curcumin's scavenging of reactive oxygen species (ROS), a phenoxyl radical is formed, depleting the curcumin. Vitamin C (ascorbic acid) provides the necessary hydrogen ion to allow regeneration of the curcumin molecule, thus extending its operating life and essentially increasing the effective curcumin concentration in the composition. Because of the reformation of the curcumin by the hydrogen donor capability of Vitamin C, the curcumin and/or ginger can be at concentrations below pharmaceutical grade. Furthermore, the water soluble ascorbic acid and curcumin, which is lipid soluble, synergistically extend the lifetime of each of the scavengers. These two molecules, curcumin and Vitamin C (ascorbic acid), when present together will facilitate the formation of the collagen and aid in UV protection.

Vitamin D, not technically a vitamin, is a fat-soluble steroid that can be considered a hormone, as it produces biological effects using nuclear receptors in the body. Vitamin D affects the concentration of calcium and phosphate in the blood, promoting healthy cell growth, neuromuscular and immune functions, and reduction of inflammation, and remodeling of bone. It should be understood that although the term "Vitamin D" is used herein that all forms of Vitamin D, including Vitamin $D_2$, Vitamin $D_3$, are included.

Vitamin E is a fat-soluble (lipid soluble) antioxidant, acting as a peroxyl radical scavenger, inhibiting the production of free radicals. Vitamin E can be absorbed into cells, protecting them from damage and promoting healthy cell growth, including wound healing.

Any of the listed additives may have additional specific and particular benefits that are not discussed or described herein; this should not be taken in any manner as a detriment to their beneficial effects as an additive to compositions having ginger-curcumin.

The combination on one or more of the above identified additives with the ginger-curcumin, when used in a topical formulation applied to human skin, produces additional unexpected synergistic benefit(s) over the ginger-curcumin benefits of slowing the detrimental effects of skin aging such as purpura, thinning of the skin, reducing wrinkles, and increasing poor or slow wound repair. Compositions having one or more of hyaluronic acid, glutathione, methylsulfonylmethane (MSM), Vitamin C, sodium lauryl sulfate, Vitamin D and Vitamin E, and ginger-curcumin, significantly improve skin quality and decrease skin aging, as compared to ginger-curcumin without these additives. Additionally, compositions having one or more of hyaluronic acid, glutathione, methylsulfonylmethane (MSM), Vitamin C, and sodium lauryl sulfate, one or both of Vitamin D and Vitamin E, and ginger-curcumin, significantly improve skin quality and decrease skin aging, as compared to ginger-curcumin without any of these additives and as compared to the composition without the Vitamin D and/or Vitamin E. Still further, compositions having one or more of hyaluronic acid, glutathione, methylsulfonylmethane (MSM), Vitamin D, and sodium lauryl sulfate, both of Vitamin C and Vitamin E, and ginger-curcumin, are particularly useful in skin rejuvenation. Because Vitamin C is a water soluble antioxidant and scavenger, and Vitamin E is a fat soluble antioxidant, the presence of both Vitamin E and Vitamin C will act synergistically to facilitate skin rejuvenation.

The composition is a compound formulated to be topically applied to human skin. In some implementations, the composition is a compound formulated to be topically applied to animal (e.g., mammal) skin. Examples of animals that would benefit from such a composition include dogs, cats, rats, mice, horses and cattle.

The ginger can be present at a level of at least 0.01 wt-% of the total composition, and similarly the curcumin can be present at a level of at least 0.01 wt-% of the total composition. Additionally, the ginger can be present at a level of no more than 15 wt-% of the total composition, and similarly the curcumin can be present at a level of no more than 15 wt-% of the total composition. More than one type of ginger and/or curcumin may be present. Example compositions include about 1 wt-% to 15 wt-% curcumin and about 0.1% to about 10 wt-% ginger; one specific example has about 10 wt-% curcumin and about 3 wt-% ginger. Because of the presence of the additives according to this disclosure and their synergistic effect with ginger and curcumin, the ginger and curcumin can be at concentrations below pharmaceutical grade.

The ginger:curcumin may be present in ratios ranging from 10:1 to 1:10; more ginger than curcumin may be present, more curcumin than ginger may be present, or their amounts may be the same.

The composition also includes one or more of hyaluronic acid, glutathione, methylsulfonylmethane (MSM), sodium lauryl sulfate (SLS), Vitamin C (ascorbic acid), Vitamin D and Vitamin E. The amount of additive(s) in the compositions is at least 0.005 wt-%, at least 0.01 wt-%, at least 0.05 wt-% or even at least 0.1 wt-% of the composition; in some implementations, the amount of each additive present is at least 0.005 wt-% or 0.01 wt-% or 0.1 wt-% of the composition. Additionally or alternately, the amount of additive(s) in the compositions is at least 1 wt-%, at least 5 wt-% or even at least 10 wt-% of the ginger-curcumin; in some implementations, the amount of each additive present is at least 0.1 wt-% or 1 wt-% of the ginger-curcumin.

The carrier for the ginger-curcumin and the additive(s) can be a lotion, cream, salve, ointment, paste, gel, serum or other semi-solid carrier that can readily be applied to and optionally spread on to the skin. In some implementations, the carrier may be a liquid solvent (e.g., an aqueous solvent); liquid formulations can be applied by spraying.

Any number of adjuvants may be present in the carrier, adjuvants such as emollient(s) (e.g., lanolin, coconut oil, cocoa butter, jojoba oil, avocado oil), moisturizer(s), humectant(s), binder(s), thickener(s), filler(s), preservative(s), stabilizer(s), fragrance(s), antioxidant(s), anti-inflammatory(s), conditioning agent(s), and UV blocker(s). Such adjuvants would typically include, e.g., one or more of stearyl alcohol, glyceryl monostearate, polyoxyl 40 stearate, isopropyl palmitate, paraffin, glycerin, lactic acid, potassium sorbate, and purified water. For wound healing, an antibiotic adjuvant and/or antibacterial adjuvant may be present. The inclusion of retinoids and retinols can be avoided. The adjuvants may be the same or different for compositions for humans compared to compositions for animals. As an example, compositions for animals may include any or all of a pesticide(s), fungicide(s), and deodorant(s).

The ginger-curcumin, additive(s), carrier and any optional ingredients can be combined using any technique suitable to incorporate the various ingredients. Depending on the carrier, the additives(s) and the ginger-curcumin are homogeneous throughout the carrier and should not settle, clump, agglomerate, or otherwise result in an undesirable consistency.

The formulated composition may be stored at room temperature or refrigerated, based on the requirements of the carrier.

Typically, the composition will be applied to the skin to be treated at room temperature, although in some situations (e.g., a spa setting) the composition may be applied at elevated temperature and/or humidity.

The following combinations of ingredients were found to be particularly useful when compounded into compositions:

One or more of glutathione, MSM, Vitamin C, hyaluronic acid, and sodium lauryl sulfate, in concentrations of each ingredient ranging from 0.005-15%, in some implementations 0.1-15%, when mixed with ginger-curcumin, provided a synergistic effect increasing the effectiveness of the ginger-curcumin on skin to increase collagen, procollagen, and decrease matrix metalloproteinase. The effect was particularly evident when all of glutathione, MSM, Vitamin C, hyaluronic acid, and sodium lauryl sulfate were present; the effect was also evident when MSM, Vitamin C, hyaluronic acid, and sodium lauryl sulfate were present.

Glutathione, MSM and Vitamin C, in concentrations of each ingredient ranging from 0.005-15.0%, in some implementations 0.01-15.0%, provided a synergistic effect on the positive effects of ginger-curcumin extract on skin to increase collagen, procollagen, and decrease matrix metalloproteinase.

MSM and hyaluronic acid, in concentration ranging from 0.005-15%, in some implementations 0.1-15%, provided a synergistic effect on the positive effects of ginger-curcumin and ginger-curcumin extract on skin to increase collage, procollagen, and decrease matrix metalloproteinase.

Glutathione, MSM, Vitamin C, and hyaluronic acid, in concentrations of each ingredient ranging from 0.005-15%, in some implementations 0.1-15%, provided a synergistic effect of achieving higher utilization of the ginger-curcumin and more rapid skin healing, by facilitating and expediting the growth of collagen and procollagen, and decreased matrix metalloproteinase.

Glutathione, MSM, Vitamin C, hyaluronic acid and sodium lauryl sulfate added to ginger-curcumin or ginger-curcumin extract increased procollagen, collagen, promoted cellular growth, and supported fibroblast growth and health. As previously stated, the positive effects of increased collagen and fibroblasts thus mitigate the effects of skin aging resulting in skin thickening, decreased formation of purpura, and shortening the time of wound healing. The addition of Vitamin D and/or Vitamin E may further increase skin thickness, decrease the formation of purpura, and shorten the time of wound healing.

MSM and hyaluronic acid, each in concentration in the range of 0.005-15%, in some implementations 0.05-15% provided a synergistic effect to ginger-curcumin or ginger-curcumin extracts, by increasing collagen and fibroblasts and thus mitigating the effects of skin aging resulting in skin thickening, decreased formation of purpura, and shortening the time of wound healing, due to stimulation of collagen and increase of fibroblast formation.

Vitamin D and Vitamin E were also found to have beneficial effects on one or more of increasing skin thickness and skin rejuvenation, decreasing the formation of purpura, shortening the time of wound healing and expediting the growth of collagen, procollagen, and decreasing matrix metalloproteinase.

Numerous different compositions having ginger, curcumin and at least one of the additives described herein were made and tested.

A large set of studies was done to compare the combination of curcumin and ginger extract alone to a more complex mix containing curcumin and ginger and also containing four additives that enhance the effects of the curcumin and ginger extract by themselves. The four additional additives (reagents) tested included hyaluronan, Vitamin C (ascorbic acid), sodium lauryl sulfate (SLS) and dimethyl sulfone (MSM).

The following reagents were used in the study: curcumin, ginger extract, hyaluronan, sodium lauryl sulfate, dimethyl sulfone and ascorbic acid (Vitamin C). The curcumin used was obtained from Sigma-Aldrich (product number C1386) and was solubilized at 20 mg/mL in DMSO. The ginger used was ginger extract as a $CO_2$ extraction of raw ginger root (from Sigma-Aldrich; product number W252108) that was diluted 1:10 in DMSO. Hyaluronan was purchased from R&D Systems. The lot used has a molecular weight range of 75-350 kDa. Hyaluronan was solubilized directly in a serum-free culture medium (Keratinocyte Basal Medium, "KBM") at 2 mg/mL. Sodium lauryl sulfate (aka, sodium dodecyl sulfate) was obtained from Sigma-Aldrich (product number 43613) and was solubilized in DMSO at a concentration of 20 mg/mL. Dimethyl sulfone (MSM) was obtained from Sigma-Aldrich (product number M81705) and dissolved in culture medium at a concentration of 20 mg/mL. L-ascorbic acid (Vitamin C) was obtained from Sigma-Aldrich (product number A0287) and was dissolved directly in KBM at a concentration of 20 mg/mL.

Each of the six reagents was initially tested (individually) over a wide range of concentrations in the human dermal fibroblast cytotoxicity assay. After concentrations with cytotoxic (or growth-suppressing) activity were identified, the levels were "backed off" by a half-log and the six reagents were mixed together—keeping the solvent, DMSO, constant and at a low concentration (1.35 µl/mL) that had no activity on its own. Concentrations of the mix that had no cytotoxic/growth-inhibiting effects were tested for activity in the fibroblast survival assay. The combination of curcumin and ginger (alone) was compared to the mix of six reagents (curcumin and ginger plus the four additives) in the fibroblast survival assay. The 6-reagent mix (curcumin and ginger plus the four additives, MSM, SLS, Vitamin C and hyaluronan) and the 4-reagent mix (curcumin and ginger plus two additives, MSM and SLS) were tested in the human skin organ culture assay. The curcumin-ginger mix alone served as control.

Fibroblast Culture Protocol.

Human dermal fibroblasts were isolated from skin biopsies and grown in monolayer culture using DMEM supplemented with 10% fetal bovine serum as culture medium. Growth was at 37° C. in a humidified atmosphere containing 5% $CO_2$ and 95% air. For experimental studies, cells were plated at $5 \times 10^4$ cells per well in wells of a 24-well culture dish in the same culture medium. One day later, cells were washed and the DMEM culture medium was replaced with KBM.

Fibroblast Cytotoxicity Assay.

Human dermal fibroblasts were treated with culture medium (KBM) supplemented with a concentration of calcium (1.5 mM) that supports fibroblast survival on its own. Reagents to be tested for cytotoxicity and/or growth inhibition were included in the culture medium and the cells incubated for 72 hours. Under control conditions (i.e., in the absence of any additional agent), there was little net increase in growth (since this was a basal medium) but cell survival was almost 100%. For each of the reagents used here, the highest concentration that did not reduce cell numbers relative to control was identified.

Fibroblast Survival Assay.

This assay has validity as a screening assay for skin-repair potential. This assay was similar to the fibroblast cytotoxicity assay except that human dermal fibroblasts were incubated in culture medium (KBM) supplemented with a concentration of calcium (0.1 mM) that does not support fibroblast survival on its own. Using these conditions, the capacity of a reagent to prevent fibroblast cell death was identified. Each of the reagents used was assessed for activity in this assay. The same concentrations of ATRA (all-trans retinoic acid) that have activity in this assay also improve collagen production by modulating the activity of the major collagen-degrading enzymes, the matrix metalloproteinases (MMP-1). The concentrations that are effective in this assay (1-10 µM) are the concentrations that reach the viable portion of the epidermis when a therapeutic dose is applied topically to healthy, intact skin.

Studies with Human Skin in Organ Culture.

For organ culture experiments, 12 2-mm full thickness punch biopsies of sun-protected hip skin from normal skin donors were obtained (donors between 18-70 years of age). The biopsies were incubated in wells of a 24-well dish (one tissue piece per 0.5 mL of culture medium). The organ cultures were incubated in KBM supplemented with Ca' to the same final concentration (1.5 mM) as used with fibroblasts. The reagents to be tested were included in the culture medium. Other than to provide a small amount of medium, nothing further was done to maintain an air-liquid interface. The tissue was incubated at 37° C. in an atmosphere of 95% air and 5% $CO_2$.

Freshly-obtained skin samples were placed in culture and immediately treated with the 4-reagent mix (1×) or with the 6-reagent mix at 0.1×. Curcumin-ginger (0.1×) served as control. Fresh medium and treatments were provided at the initiation of the culture and at 2-day intervals over an eight day incubation period. At the end of the incubation period (day-8), the tissue was fixed in buffered formalin, stained with hematoxylin & eosin, and evaluated for histological features. Conditioned culture fluid obtained at each treatment period (days 2, 4, 6 and 8) was collected. Individual ELISA tests were used to assess the same culture fluids for type I procollagen, matrix metalloproteinase-1 (MMP-1) and tissue inhibitor of metalloproteinases-1 (TIMP-1). Although organ culture fluid was collected at each time-point, only the two-day culture fluids were tested for the biomarkers.

Results

Monolayer Culture Studies.

In the initial studies, each of the six agents was tested individually in the fibroblast cytotoxicity assay. With four of the six agents (i.e., curcumin, ginger extract, SLS and MSM), levels that produced growth-inhibition/cytotoxicity were achieved. In contrast, Vitamin C and hyaluronan proved to be non-toxic at all concentrations evaluated (up to 200 µg/mL for L-ascorbic acid and 20 µg/mL for hyaluronan). Table 1 presents the concentrations of each agent that went into the 6-reagent mix; the concentration of DMSO in the formula was 1.35 µl/mL. This mix was subsequently termed "1× formulation".

TABLE 1

Concentrations of each reagent in the 1X formulation.

| Agent | Concentration in 1X formulation |
|---|---|
| Curcumin | 5 µg/mL |
| Ginger extract | 1 µl of the 10% stock in 1 mL |
| Hyaluronan | 20 µg/mL |
| L-ascorbic acid | 200 µg/mL |
| SLS | 5 µg/mL |
| MSM | 2 µg/mL |

FIG. 1 shows the titration curve of the six reagents (ginger, curcumin, SLS, MSM, Vitamin C, hyaluronan) together in the fibroblast cytotoxicity assay. After titration of each additive separately, the highest concentrations of each agent that were not cytotoxic were identified and a mix of the six additives was prepared. When all six reagents were included in the 1× formulation, there was cytotoxicity/growth-inhibition (i.e., a reduced number of cells relative to control). Several serial dilutions from the 1× formulation were prepared and tested. The 0.5× formulation as well as the 1× formulation was growth suppressing but when the 1× formulation was reduced to 0.1×, growth-suppressing activity was not seen.

Figure 2A:
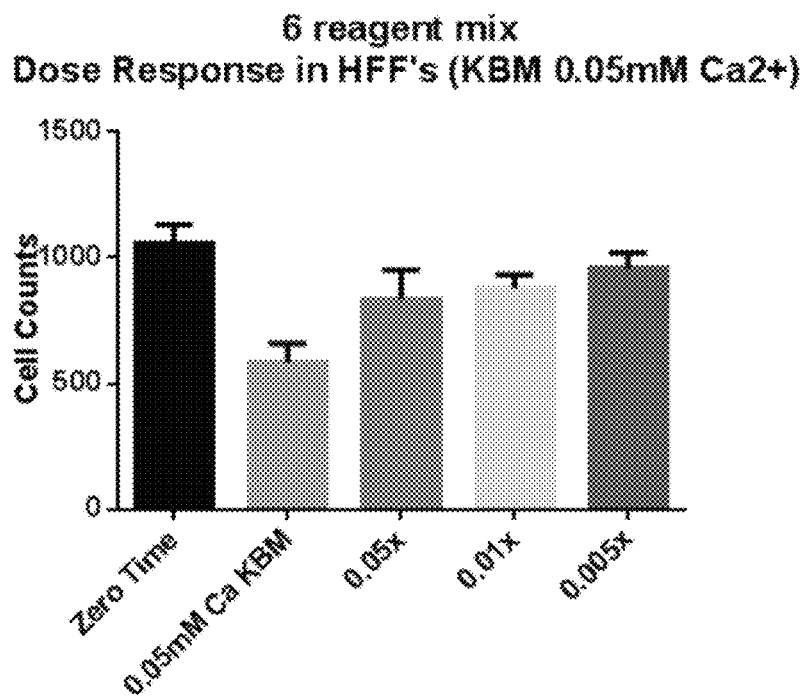
FIGS. 2A and 2B are graphical representations of titration curves for a fibroblast survival assay.
Figure 2B:
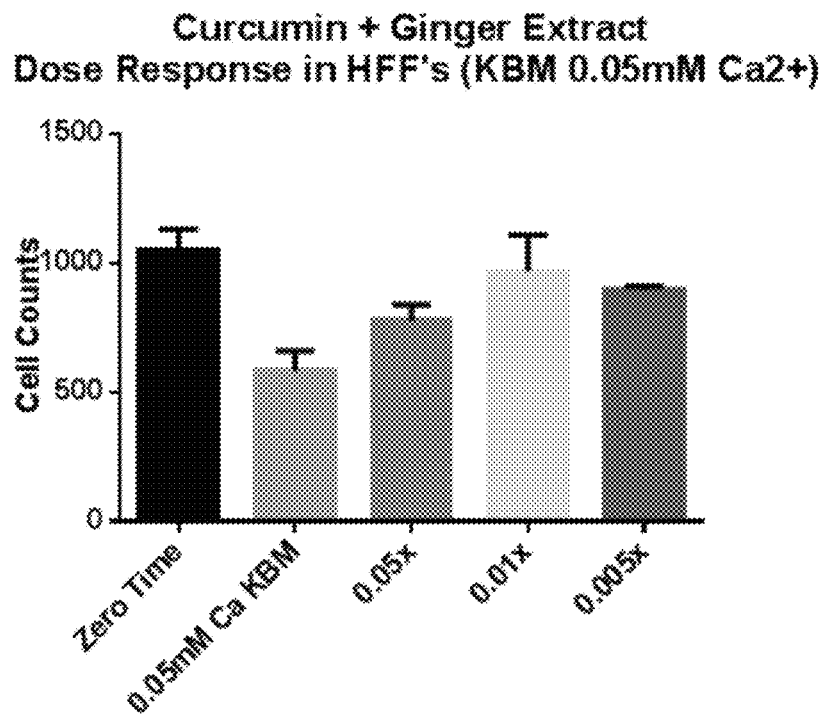

A series of studies was also done to assess the capacity of the 6-reagent mix to preserve fibroblast survival under conditions in which cell lysis would otherwise occur (fibroblast survival assay). FIG. 2A shows the titration curve of the six reagents (ginger, curcumin, SLS, MSM, Vitamin C, hyaluronan) together in the fibroblast survival assay and FIG. 2B shows the titration curve for curcumin and ginger. This assay was used to demonstrate that the mix of ginger and curcumin with four additives could be used to support fibroblast survival under conditions that would otherwise be cytotoxic. As seen here, the 0.05×-0.005× formulations were protective. Lower concentrations of the mix were also protective, but the level of protection declined with dilution (not shown).

Note that the cell counts presented in FIGS. 2A and 2B underestimate the protective value of the 6-reagent formulation. This is due to the fact that when the cells lyse (as virtually all do under control conditions), the debris is mistakenly counted in the electronic particle counter. This is substantiated in FIGS. 3A through 3D, which present phase-contrast images of the cells at the end of the incubation period. The control well (FIG. 3A) has only debris. The wells receiving the 6-reagent mix show high viability.

Figure 3A:
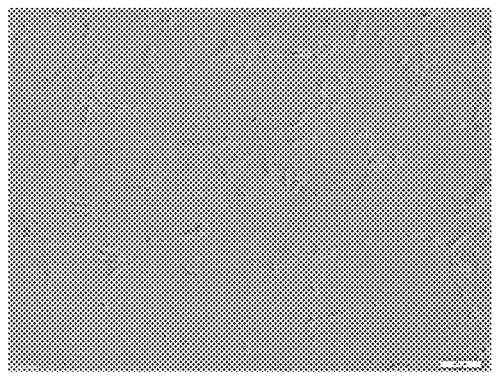
FIGS. 3A through 3D are phase-contrast photomicrographs showing the appearance of human diploid fibroblasts.
Figure 3B:
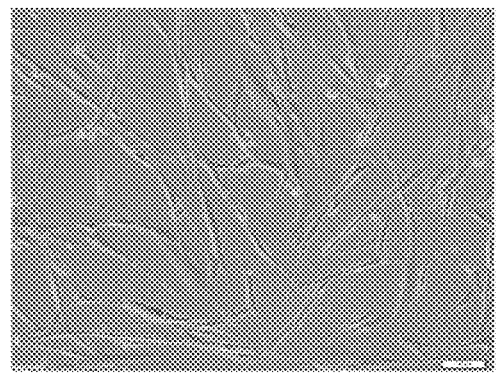
Figure 3C:
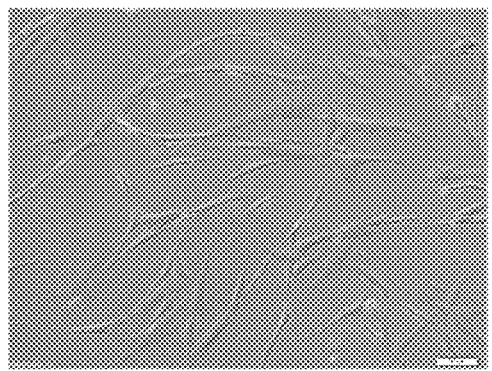
Figure 3D:
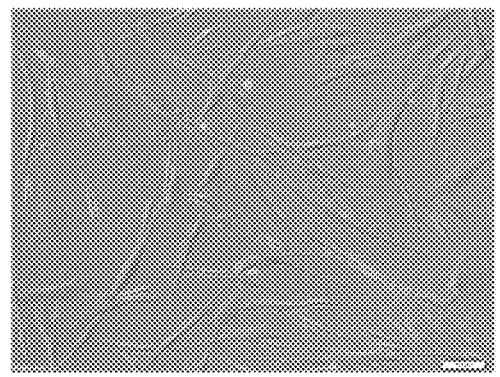

FIGS. 3A through 3D are phase-contrast photomicrographs showing the appearance of human diploid fibroblasts after 48-hours in the survival assay. FIG. 3A shows the control, where virtually all of the few remaining cells in the dish are dead. FIG. 3B is the 0.005× formulation, showing strong protection. FIG. 3C is the 0.01× formulation, showing strong protection. FIG. 3D is the 0.05× formulation, also showing strong protection.

Some studies were done to determine if the four additional agents (SLS, MSM, Vitamin C, hyaluronan) would have biological activity in the absence of curcumin and ginger extract. When used as a 1× or 0.5× formulation, there was significant protection but cell survival fell off with further dilution.

Figure 4A:
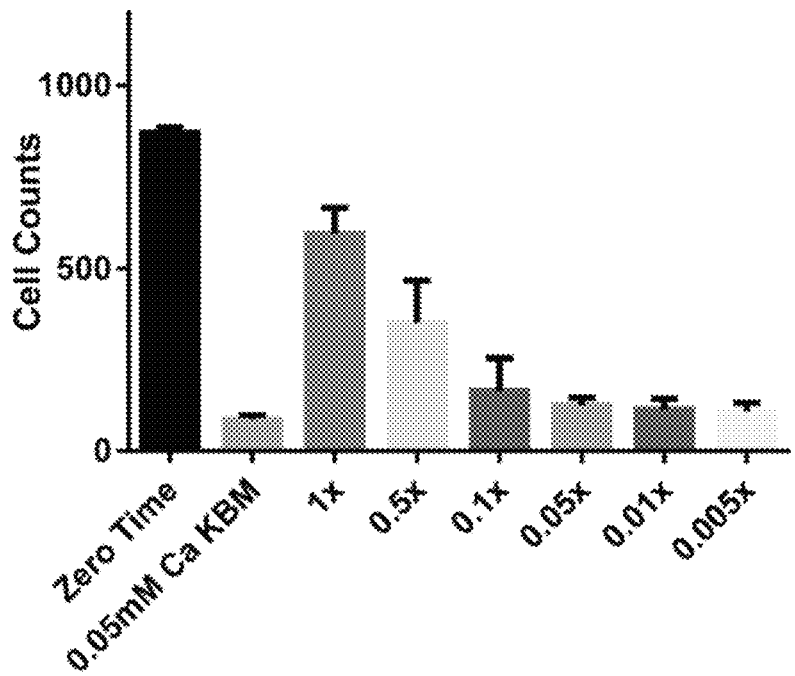
FIGS. 4A and 4B are graphical representations of titration curves for a fibroblast survival assay.
Figure 4B:
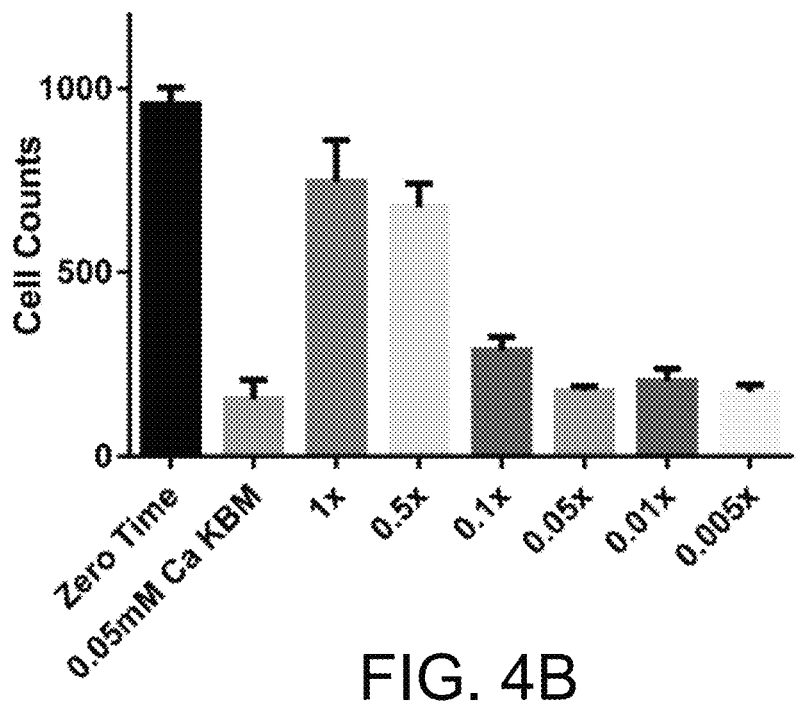

Both FIGS. 4A and 4B are the titration curve of four reagents (SLS, MSM, Vitamin C, hyaluronan) without curcumin and ginger in the fibroblast survival assay. FIG. 4A and FIG. 4B show results from duplicate experiments. This assay was used to demonstrate that the mix of these four additives, SLS, MSM, Vitamin C and hyaluronan, (without curcumin and ginger extract) could be used to support fibroblast survival under conditions that would otherwise be cytotoxic. As seen here, the mix of four regents was protective. However, the amounts used were higher than were needed when curcumin and ginger extract were also present.

The results presented in FIGS. 2A through 4B together indicate that the four reagents (SLS, MSM, Vitamin C, hyaluronan) are biologically active in the fibroblast survival assay even without ginger and curcumin.

Another set of studies was carried out in which the 4-reagent mix (hyaluronan, SLS, Vitamin C and MSM) was kept constant at the 0.05× formulation and the combination of curcumin and ginger extract was titrated into the mix. The data from this study are presented in FIG. 5 and FIGS. 6A-6G.

Figure 5:
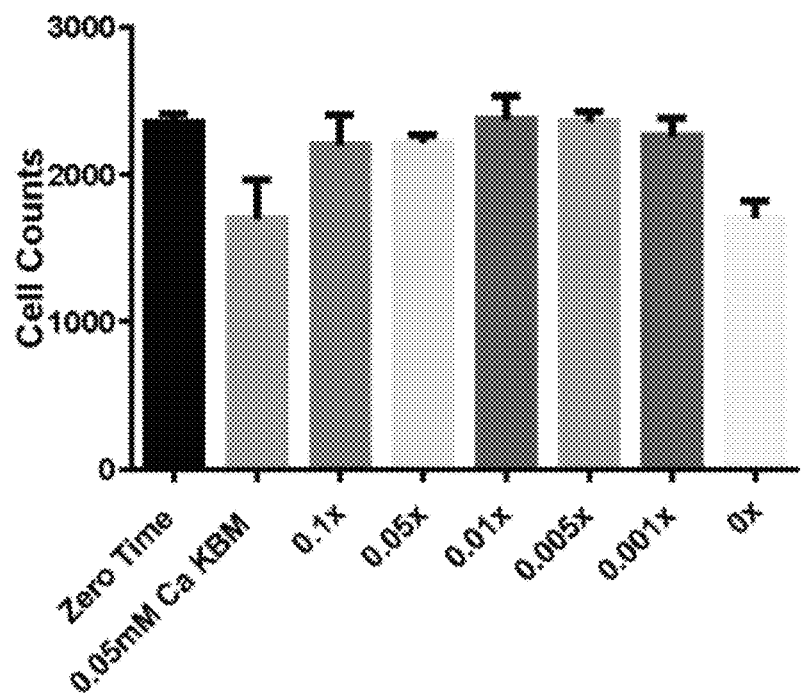
FIG. 5 is a graphical representation of a titration curve.

FIG. 5 is the titration curve of curcumin-ginger extract with the 4-reagent mix kept constant and FIGS. 6A through 6F are phase-contrast images. For this assay, the 4-reagent mix was kept constant at 0.5×. Then, the combination of curcumin-ginger extract was titrated downward, starting from the 0.1× formulation.

Figure 6A:
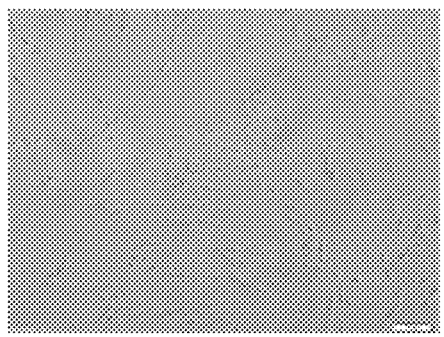
FIGS. 6A through 6G are phase-contrast photomicrographs for the titration curve of FIG. 5.
Figure 6B:
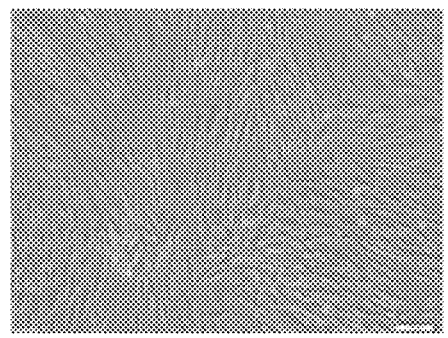
Figure 6C:
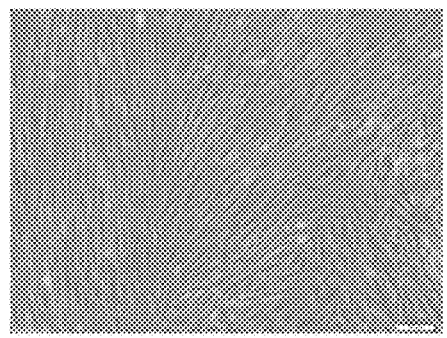
Figure 6D:
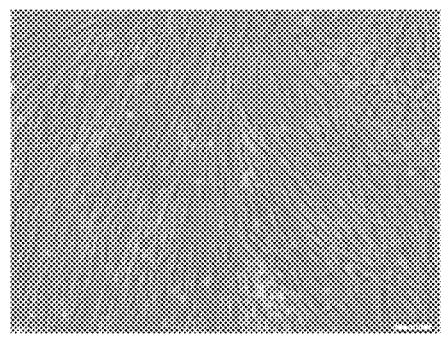
Figure 6E:
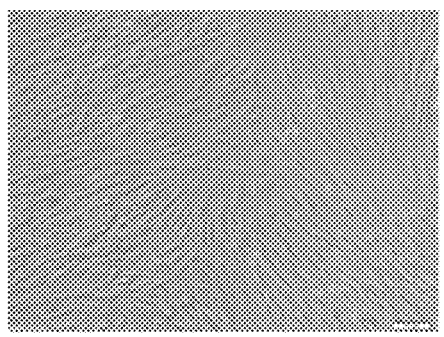
Figure 6F:
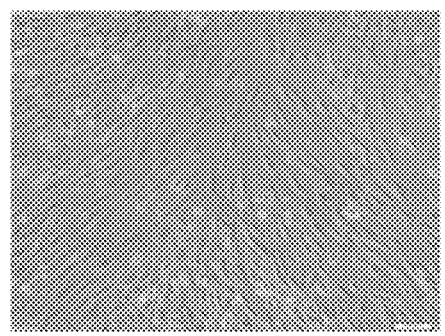
Figure 6G:
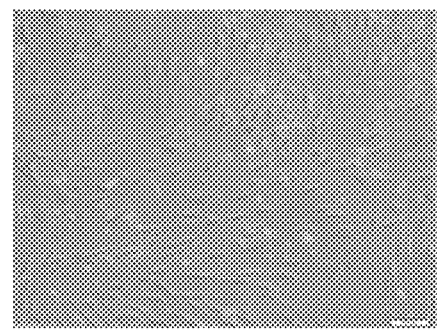

FIG. 6A shows the control, having 0.05 mM Ca+2 and KBM; FIG. 6B shows 0.1× curcumin and ginger; FIG. 6C shows 0.05× curcumin and ginger; FIG. 6D shows 0.01× curcumin and ginger; FIG. 6E shows 0.005× curcumin and ginger; FIG. 6F shows 0.001× curcumin and ginger; and FIG. 6G shows OX curcumin and ginger. To note: there is a virtually complete loss of viability in the control (seen in FIG. 6A). When there is no curcumin and ginger extract, there is viability (seen in FIG. 6G). Greater protection is observed with the combination of curcumin and ginger extract added to the mix of four reagents. Viability falls off at the 0.001 curcumin and ginger extract (seen in FIG. 6F).

This confirmed the activity of both the mix of 4-reagents alone but the added benefit of the combined mix of the reagents with ginger and curcumin.

Organ Culture Studies.

Biopsies of human, sun-protected skin were cultured for eight days under control conditions or treated with the tested compositions. For this, the 4-reagent mix was used at 1× while the 6-reagent mix was used at 0.1× and 0.05×. Curcumin-ginger alone was used at 0.1× and 0.05× for control. Culture fluids collected on day-2 were assessed by ELISA tests for levels of type I procollagen, MMP-1 and TIMP-1. At the end of the incubation period, the tissue biopsies were fixed in 10% buffered formalin and prepared for histology. Table 2 shows ELISA test results. The values for "control" were set at 1.0 and values from other conditions represent fold-change relative to control. Values are mean±SD.

TABLE 2

Type I procollagen, MMP-1 and TIMP-1 in organ culture fluids.

| Treatment group | Procollagen | MMP-1 | TIMP-1 |
|---|---|---|---|
| Control | 1.0 | 1.0 | ND |
| 4-reagent mix (1X) | 1.3 ± 0.3 | 1.1 ± 0.6 | ND |
| 6-reagent mix (0.05X) | 1.6 ± 1.1 | 0.8 ± 0.4 | ND |
| Curcumin-ginger (0.05X) | 1.5 ± 1.3 | 0.8 ± 0.2 | ND |
| 6-reagent mix (0.1X) | 2.0 ± 1.2 | 0.7 ± 0.2 | ND |
| Curcumin-ginger (0.1X) | 2.3 ± 1.3 | 0.5 ± 0.4 | ND |

It can be seen from Table 2 that the 4-reagent mix demonstrated a slight increase in the level of type I procollagen relative to control. While not statistically significant (with n=4 biopsies from 2 subjects, this is not unexpected), the data are suggestive. Table 2 also demonstrates that both the 6-reagent mix and curcumin-ginger alone increased type I procollagen to a much greater extent and decreased the level of MMP-1, the enzyme most responsible for collagen degradation in the skin. TIMP-1 was not detected for any of the formulations.

FIGS. 7A through 7F and FIGS. 8A through 8F show the histological appearance of human skin in organ culture, with FIGS. 7A through 7F showing epidermal features and FIGS. 8A through 8F showing dermal features.

Figure 7A:
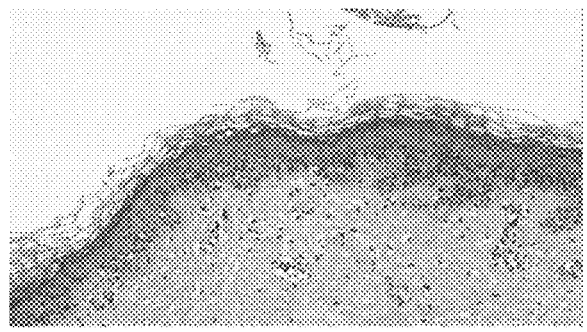
FIGS. 7A through 7F are photomicrographs of human skin showing epidermal features.
Figure 7B:
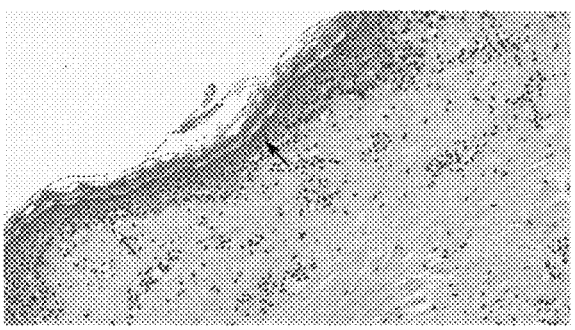
Figure 7C:
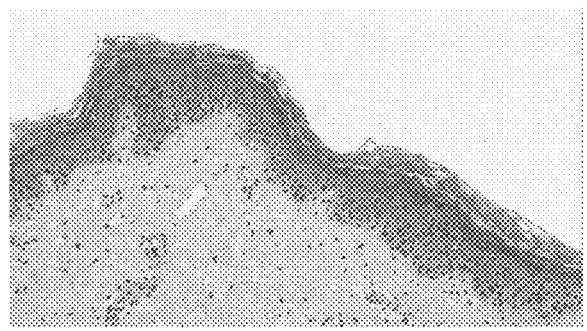
Figure 7D:
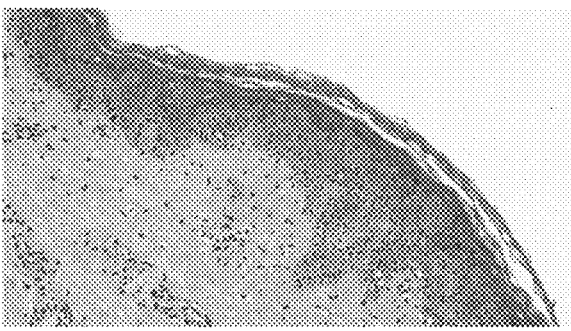
Figure 7E:
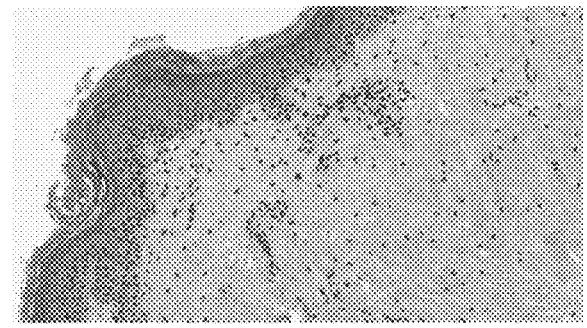
Figure 7F:
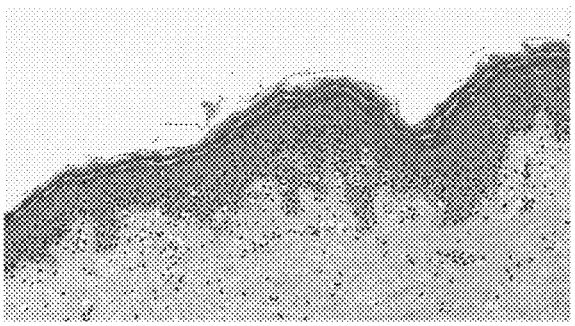
Figure 8A:
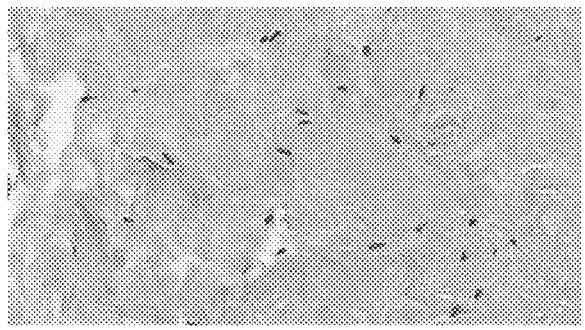
FIGS. 8A through 8F are histological photomicrographs of human skin showing dermal features.
Figure 8B:
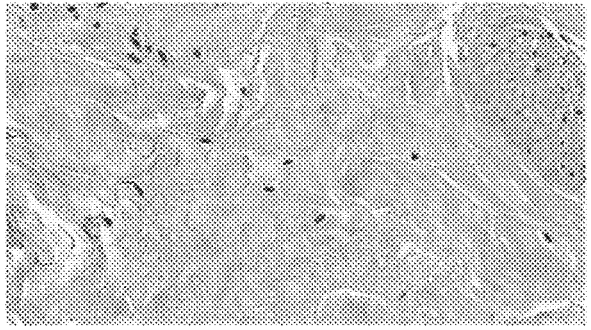
Figure 8C:
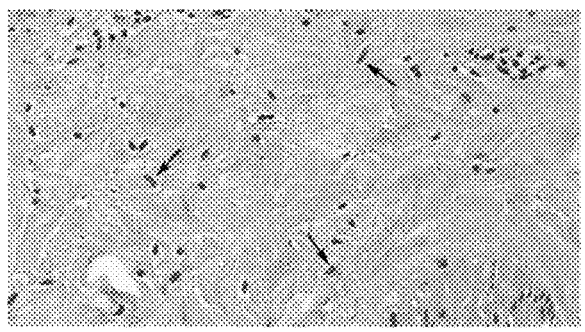
Figure 8D:
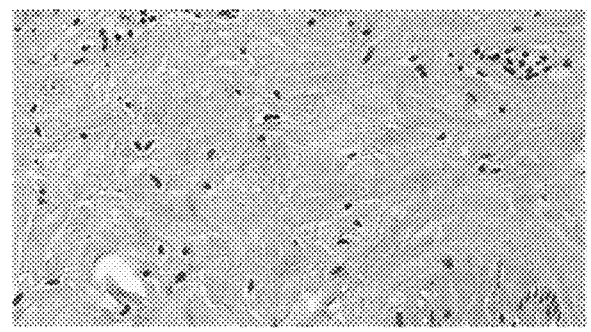
Figure 8E:
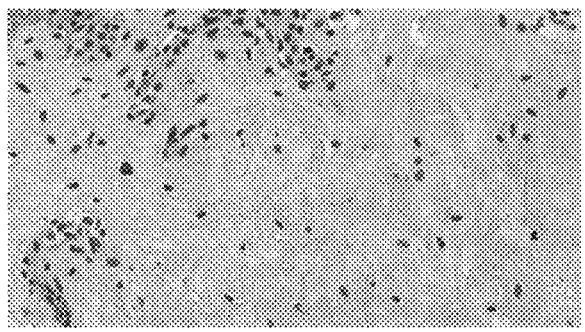
Figure 8F:
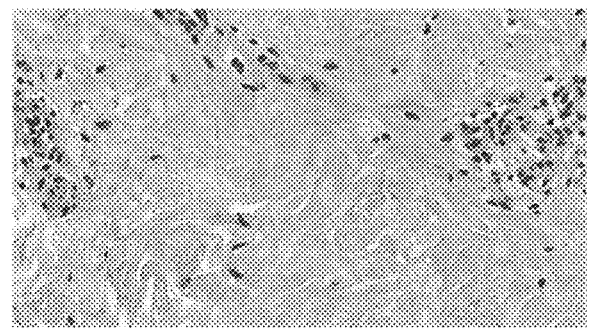

The human skin was maintained for 8-days in organ culture during which time it was treated as noted below. At the end of the incubation period, the skin biopsies were examined histologically after staining with hematoxylin and eosin. FIGS. 7A and 8A: Control. FIGS. 7B and 8B: 4-reagent (ginger, curcumin, SLS, MSM) mix (1×). The white arrow in FIG. 7B points to an area of basal epithelium with vacuolated cell and the black arrow points to an area in upper epidermis with pycnotic nuclei. FIGS. 7C and 8C: 6-reagent (ginger, curcumin, SLS, MSM, Vitamin C, hyaluronan) mix (0.05×). In FIG. 8C, the arrows point to nuclei of activated cells. FIGS. 7D and 8D: curcumin-ginger (0.05×). FIGS. 7E and 8E: 6-reagent mix (0.1×). FIGS. 7F and 8F: curcumin-ginger (0.1×).

After 8 days in culture, the control skin (FIG. 7A) had the appearance of freshly biopsied. Skin treated with the 4-reagent mix (FIG. 7B) shows signs of toxicity in upper epidermis (i.e., presence of necrotic cells and incomplete differentiation). Skin biopsies treated with either the 6-reagent mix (FIG. 7C) or with curcumin and ginger at either concentration (FIGS. 7D and 7F) show evidence of mild to moderate hyperplasia (i.e., epidermal thickening). The appearance of the skin treated with the 6-reagent mix (FIG. 7C) or with the curcumin-ginger combination (FIGS. 7D and 7F) is indistinguishable.

Also after 8 days in culture, healthy dermal fibroblasts can be seen throughout the dermis (identified by the blue-appearing nuclei). Fibroblasts can also be seen in the dermis of the skin treated with the 4-reagent mix (FIG. 8B). There is no apparent toxicity. Fibroblasts can also be seen throughout the dermis of the skin biopsies treated with the 6-reagent mix (FIG. 8C) or with the curcumin-ginger combination (FIGS. 8D and 8F). The number of nuclei seen in these sections is increased as compared to control (FIG. 8A) and many of the nuclei have an oblong "plump" appearance—indicative of activated cells. There appear to be more cells in the 6-additive mix treated skin (FIG. 8C) than in skin treated with curcumin-ginger alone.

The above specification and examples provide a complete description of the structure and use of exemplary implementations of the invention. The above description provides specific implementations. It is to be understood that other implementations are contemplated and may be made without departing from the scope or spirit of the present disclosure. The above detailed description, therefore, is not to be taken in a limiting sense. While the present disclosure is not so limited, an appreciation of various aspects of the disclosure will be gained through a discussion of the examples provided.

Unless otherwise indicated, all numbers expressing feature sizes, amounts, and physical properties are to be understood as being modified by the term "about," whether or not the term "about" is immediately present. Accordingly, unless indicated to the contrary, the numerical parameters set forth are approximations that can vary depending upon the desired properties sought to be obtained by those skilled in the art utilizing the teachings disclosed herein.

As used herein, the singular forms "a", "an", and "the" encompass implementations having plural referents, unless the content clearly dictates otherwise. As used in this specification and the appended claims, the term "or" is generally employed in its sense including "and/or" unless the content clearly dictates otherwise.

Since many implementations of the invention can be made without departing from the spirit and scope of the invention, the invention resides in the claims hereinafter appended. Furthermore, structural features of the different implementations may be combined in yet another implementation without departing from the recited claims.

What is claimed is:

1. A topical composition for application to skin, the composition comprising ginger, curcumin, dimethyl sulfone (MSM), Vitamin C, hyaluronic acid, sodium lauryl sulfate (SLS), and a carrier.

2. The composition of claim 1 further comprising glutathione.

3. The composition of claim 1 further comprising at least one of Vitamin D and Vitamin E.

4. The composition of claim 1 further comprising glutathione, Vitamin D, and Vitamin E.

5. The composition of claim 1 further comprising glutathione and at least one of Vitamin D and Vitamin E.

6. The composition of claim 1, wherein the carrier is a semi-solid carrier.

7. The composition of claim 1, wherein each of the ginger, curcumin, dimethyl sulfone (MSM), Vitamin C, hyaluronic acid, and sodium lauryl sulfate (SLS) is individually present at a concentration of 0.005%-15 wt-% of the total composition.

8. The composition of claim 7 further comprising glutathione, wherein the glutathione is individually present at a concentration of 0.005%-15 wt-% of the total composition.

9. The composition of claim 7 further comprising at least one of Vitamin D and Vitamin E, wherein each of the Vitamin D and Vitamin E, if present, is individually present at a concentration of 0.005%-15 wt-% of the total composition.

10. The composition of claim 7 further comprising glutathione, Vitamin D, and Vitamin E, wherein each of the glutathione, Vitamin D, and Vitamin E is individually present at a concentration of 0.005%-15 wt-% of the total composition.

11. The composition of claim 7 further comprising glutathione and at least one of Vitamin D and Vitamin E, wherein the glutathione and each of the Vitamin D and Vitamin E, if present, is individually present at a concentration of 0.005%-15 wt-% of the total composition.

12. The composition of claim 7, wherein the carrier is a semi-solid carrier.

13. A topical composition for application to skin, the composition comprising ginger, curcumin, dimethyl sulfone (MSM), Vitamin C, hyaluronic acid, a detergent, and a carrier.

14. The composition of claim 13 further comprising glutathione.

15. The composition of claim 13 further comprising at least one of Vitamin D and Vitamin E.

16. The composition of claim 13 further comprising glutathione, Vitamin D, and Vitamin E.

17. The composition of claim 13 further comprising glutathione and at least one of Vitamin D and Vitamin E.

18. The composition of claim 13, wherein the carrier is a semi-solid carrier.

19. The composition of claim 13, wherein each of the ginger, curcumin, dimethyl sulfone (MSM), Vitamin C, hyaluronic acid, and detergent is individually present at a concentration of 0.005%-15 wt-% of the total composition.

20. The composition of claim 19 further comprising glutathione, wherein the glutathione is individually present at a concentration of 0.005%-15 wt-% of the total composition.

21. The composition of claim 19 further comprising at least one of Vitamin D and Vitamin E, wherein each of the Vitamin D and Vitamin E, if present, is individually present at a concentration of 0.005%-15 wt-% of the total composition.

22. The composition of claim 19 further comprising glutathione, Vitamin D, and Vitamin E, wherein each of the glutathione, Vitamin D, and Vitamin E is individually present at a concentration of 0.005%-15 wt-% of the total composition.

23. The composition of claim 19 further comprising glutathione and at least one of Vitamin D and Vitamin E, wherein the glutathione and each of the Vitamin D and Vitamin E, if present, is individually present at a concentration of 0.005%-15 wt-% of the total composition.

24. The composition of claim 19, wherein the carrier is a semi-solid carrier.

* * * * *